(12) United States Patent
Vigano' et al.

(10) Patent No.: US 7,405,324 B2
(45) Date of Patent: Jul. 29, 2008

(54) PROCESS FOR SYNTHESISING AMINOADAMANTANES

(75) Inventors: Enrico Vigano', Lurago d'Erba (IT); Ernesto Landonio, Rescaldina (IT); Simona Lanfranconi, Montano Lucino (IT); Renato Molteni, Inverigo (IT)

(73) Assignee: A.M.S.A. Anonima Materie Sintetiche E. Afini S.p.A., Milan (IT)

( * ) Notice: Subject to any disclaimer, the term of this patent is extended or adjusted under 35 U.S.C. 154(b) by 56 days.

(21) Appl. No.: 11/431,175

(22) Filed: May 10, 2006

(65) Prior Publication Data

US 2006/0258885 A1     Nov. 16, 2006

(30) Foreign Application Priority Data

May 10, 2005  (IT) .......................... MI2005A0833

(51) Int. Cl.
*C07C 231/02*  (2006.01)
*C07C 233/05*  (2006.01)

(52) U.S. Cl. .................. 564/217; 564/130; 564/446; 564/448; 564/458

(58) Field of Classification Search ................ 564/130, 564/446, 448, 458, 217
See application file for complete search history.

(56) References Cited

U.S. PATENT DOCUMENTS

| 3,391,142 | A |   | 7/1968  | Mills et al. |
| 4,122,193 | A |   | 10/1978 | Scherm et al. |
| 4,663,481 | A | * | 5/1987  | Jones .......................... 564/124 |
| 5,061,703 | A |   | 10/1991 | Bormann et al. |

FOREIGN PATENT DOCUMENTS

| WO | WO 2005/062724 A2 | 7/2005 |
| WO | WO 2006/010362 A1 | 2/2006 |
| WO | WO 2006/076560 A1 | 7/2006 |
| WO | WO 2006/076562 A1 | 7/2006 |

\* cited by examiner

*Primary Examiner*—Shailendra Kumar
(74) *Attorney, Agent, or Firm*—Stetina Brunda Garred & Brucker

(57) ABSTRACT

The present invention concerns a new process for synthesising aminoadamantanes of formula I

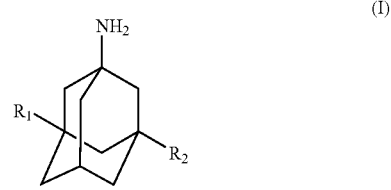

(I)

in which R1 and R2 are identical or different and are H or a straight or branched alkyl group comprising from 1 to 6 carbon atoms, and addition salts thereof with inorganic or organic acids, in particular memantine hydrochloride (1-amino-3,5-dimethyladamantane hydrochloride).

21 Claims, 1 Drawing Sheet

PROCESS FOR SYNTHESISING AMINOADAMANTANES

CROSS-REFERENCE TO RELATED APPLICATIONS

Not Applicable

STATEMENT RE: FEDERALLY SPONSORED RESEARCH/DEVELOPMENT

Not Applicable

FIELD OF THE INVENTION

The present invention concerns a new process for synthesising aminoadamantanes of formula (I)

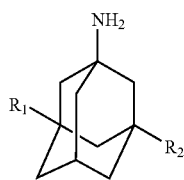

(I)

in which R1 and R2 are identical or different and are H or a straight or branched alkyl group comprising from 1 to 6 carbon atoms, and addition salts thereof with inorganic or organic acids, in particular memantine hydrochloride (1-amino-3,5-dimethyladamantane hydrochloride). Many tri- and tetra substituted adamantanes are known to have an activity on the central nervous system, being effective for treating Parkinson's Disease in particular.

Among these, memantine hydrochloride is a known N-methyl-D-aspartic acid (NDMA) receptor antagonist, and as such is used for preparing proprietary drugs for treating various mental illnesses.

BACKGROUND

An early synthesis of the aforesaid substituted aminoadamantanes, in particular memantine hydrochloride, starting from its precursor 1-bromo-3,5-dimethyladamantane was described in U.S. Pat. No. 3,391,142. This synthesis protocol comprises, in the first step, the reaction between 1-bromo-3,5-dimethyladamantane and large excesses of both acetonitrile and concentrated sulfuric acid, to provide 1-acetamido-3,5-dimethyladamantane by way of the so called Ritter reaction. This reaction, which proceeds via the attack of an acetonitrile on a carbocation that forms in an acid environment followed by formation of an amide, is strongly exothermic, with consequent scale-up problems as the reactors normally used for synthesising pharmaceutical active principles are not designed to dissipate such developed heat. This is because they have in reality to be suitably over-dimensioned in order to be able to handle without serious dangers eventual extreme heat release peaks caused by potential reagent accumulations in the system. In the case of U.S. Pat. No. 3,391,142, also the second synthesis step described therein which leads from the 1-acetamido-3,5-dimethyladamantane to the final product, has shown to be problematic, in that the hydrolysis of 1-acetamido-3,5-dimethyladarnantane is undertaken in the presence of sodium hydroxide in diethylene glycol heated under reflux, i.e. at temperatures exceeding 245° to 250° C. for at least 6 hours, after which the reaction product is poured onto ice. Also these conditions, given the high temperatures needed, not only require special plants, not commonly used in the synthesis of proprietary drugs, but are also very severe—with the consequent danger of impurity formation which then must be removed by often laborious purifications. Specifically referring to U.S. Pat. No. 3,391,142, the free base obtained following the hydrolysis is extracted with benzene, taken up in ether, then added with HCl to provide the addition salt, which is then re-precipitated from a mixture of alcohol and ether.

A more modem synthesis of memantine hydrochloride, this time starting from 1-chloro-3,5-dimethyladamantane, was then described in U.S. Pat. No. 4,122,193. This synthesis protocol involves, in the first step, the reaction between 1-chloro-3,5-dimethyladamantane and urea in a pressure vessel at 220° C. These are also very severe conditions, and, if the reaction is undertaken on an industrial scale, also require special plants and safety arrangements, such as pressure vessels heatable by diathermic oils, normally not used for the synthesis of pharmaceutical active principles. In addition, the conditions described can also lead to in situ degradation of the urea used (whose thermal decomposition under atmospheric conditions takes place already at temperatures greater than 132° C., leading to the formation of biuret, ammonia and hydrocyanic acid), resulting in considerable difficulties in purifying the final product which will have to comply later with the very narrow specifications required for pharmaceutical raw materials.

In addition to the 1-acetamido-3,5-dimethyladamantane known from U.S. Pat. No. 3,391,142, the analogous 1-formamide-3,5-dimethyladamantane could be a hypothetical intermediate on the synthetic route from 1-halogen-3,5-dimethyladamantane to memantine HCl. Indeed, U.S. Pat. No. 5,061,703, in respective examples 6F, 7D, 8E and 9E proposes the synthesis of different N-formyl derivatives of different alkyladamantanes by the reaction between formamide and the respective halogen derivative under formamide reflux conditions. Here also the necessary conditions are very severe and require, for scale-up, considerable plant investment and expedients on an industrial scale. This is because, at atmospheric pressure, formamide boils at 210° C. but according to the data safety sheet its decomposition, to carbon monoxide and ammonia, starts at about 180° C. Indeed, within the sphere of the experiments undertaken by the inventors of the present application, in which 1-halogen-3,5-dimethyladamantane was reacted with formamide under the preferred conditions of U.S. Pat. No. 5,061,703, formation of a dark coloured sublimate was in fact observed on the cooled walls of the reaction container, and the entire reaction mixture appeared, after the prescribed 12 hours under reflux, as a dark pitch which liquefied on heating. And indeed the presence of impurities formed during synthesis of the formamide intermediate continues until the final hydrochloride product is obtained which—if obtained by this path—is less pure.

From the aforegoing, it therefore appears that in the current state of the art there is no synthetic approach free of the aforesaid disadvantages i.e. a synthesis path for aminoadamantanes and their addition salts, in particular memantine HCl, starting from their corresponding halogenated precursors, that can be undertaken on an industrial scale under mild conditions without the need for special equipment—designed either for operating at high temperatures or for dissipating unusual heat development peaks—which provides a final product easily purifiable to purity levels customary for pharmaceutical products and not substantially contaminated with the decomposition products of reagents used upstream. From the above, it also appears that in the current state of the art there is no synthetic approach improved from a safety aspect i.e. that also avoids, in addition to the aforesaid problem of heat development peaks, the development of toxic degradation products such as ammonia, hydrocyanic acid and/or carbon monoxide.

An object of the present invention is therefore the provision of a new synthesis procedure that solves the above mentioned problems.

BRIEF SUMMARY

The inventors of the present application have found that the drawbacks of the prior art can be overcome by a new process for synthesising aminoadamantanes and their addition salts of formula I

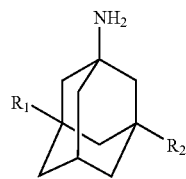

(I)

in which R1 and R2 are identical or different, and are H or a straight or branched alkyl group, comprising from 1 to 6 carbon atoms, which provides, in a first step, the synthesis of the corresponding acetamido adamantanes of formula II

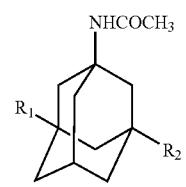

(II)

in which R1 and R2 are as above,
starting from a halogen adamantane of formula III

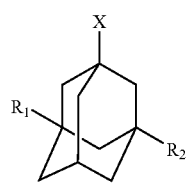

(III)

in which R1 and R2 are as above, and
in which X stands for F, Cl, Br or I,
comprising the following steps:
(a1) feeding into a reaction vessel a mixture comprising the halogen adamantane of formula III, 5-10 equivalents of acetonitrile and 5-20 equivalents of glacial acetic acid, to provide a reaction mixture,
(b1) introducing into the reaction mixture 3-10 equivalents of concentrated sulfuric acid, to provide a reacted mixture, or, alternatively:

(a2) feeding into a reaction vessel a mixture comprising the halogen adamantane of formula III, 5-20 equivalents of glacial acetic acid and 3-10 equivalents of concentrated sulfuric acid, to provide a reaction mixture,
(b2) introducing into the reaction mixture 5-10 equivalents of acetonitrile to provide a reacted mixture, and
(c) isolating the acetamido adamantane of formula II formed in step (b1) or (b2) from the reacted mixture.

The new process for synthesising aminoadamantanes and their addition salts, in particular memantine HCl, found by the inventors of the present application uses, in a second stage, hydrolysis of the acetamido adamantane comprising the following steps:
(a) feeding into a reaction vessel a mixture comprising the acetamido adamantane of formula II, 5-20 equivalents of an alkali metal or alkaline earth metal hydroxide and a solvent chosen from the group consisting of 1-methoxy-2-propanol, 2-methoxy-1-propanol, 3-methoxy-1-propanol, 2-ethoxyethanol, 2-methoxyethanol and mixtures thereof, to provide a hydrolysis mixture,
(b) heating the hydrolysis mixture under reflux for a time sufficient to achieve hydrolysis of the acetamido adamantane of formula II to give the corresponding aminoadamantane of formula I and
(c) isolating the aminoadamantane of formula I formed in step (b), preferably by conversion into an addition salt thereof.

DETAILED DESCRIPTION

Figure 1:
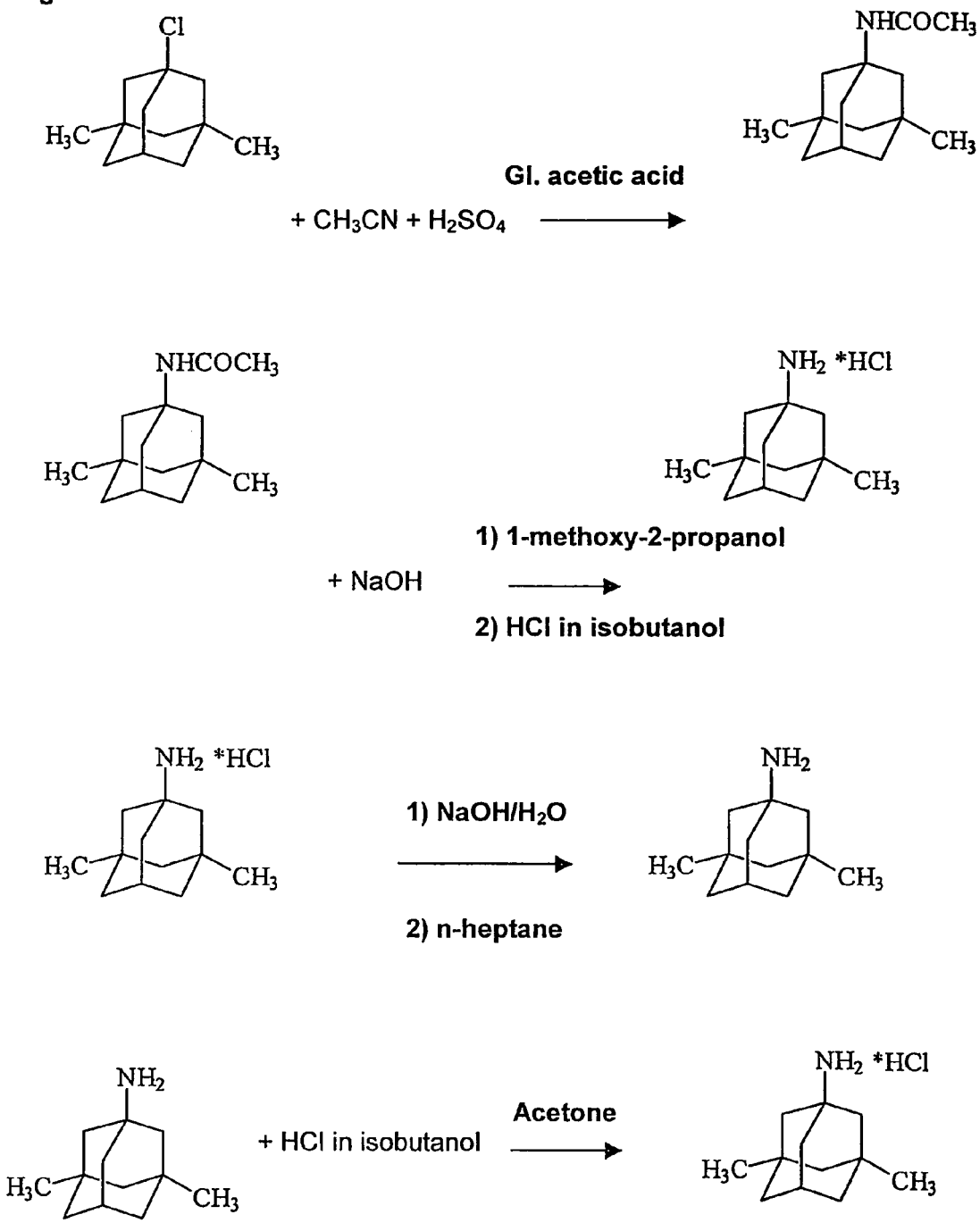
FIG. 1 is a reaction scheme which exemplifies the new process provided by the present invention, specifically regarding the synthesis of memantine HCl.

As aforedescribed, known synthesis paths to aminoadamantane involved severe conditions needing substantial plant investment, requiring among other things adequate safety measures, the elimination of toxic co-products as well as considerable effort for final product purification.

The inventors of the present application have now found that synthesis of the aminoadamantane of formula II starting from the corresponding halogen adamantanes of formula III by way of the Ritter reaction can be conducted in ordinary reactors, i.e. without special arrangements for dissipating excessive developed heat and without formation of dangerous and/or contaminating degradation products, if carried out under the conditions described herein, comprising in particular the following steps:
(a1) feeding into a reaction vessel a mixture comprising the halogen adamantane of formula III, 5-10 equivalents of acetonitrile and 5-20 equivalents of glacial acetic acid, to provide a reaction mixture,
(b1) introducing into the reaction mixture 3-10 equivalents of concentrated sulfuric acid, to provide a reacted mixture, or, alternatively:
(a2) feeding into the reaction vessel a mixture comprising the halogen adamantane of formula III, 5-20 equivalents of glacial acetic acid and 3-10 equivalents of concentrated sulfuric acid, to provide a reaction mixture,
(b2) introducing into the reaction mixture 5-10 equivalents of acetonitrile to provide a reacted mixture, and
(c) isolating the acetamido adamantane of formula II formed in step (b1) or (b2) from the reacted mixture.

In this respect, the inventors of the present invention have studied in depth the Ritter reaction as described in U.S. Pat.

No. 3,391,142, finding that the conditions described in the known art, even on a laboratory scale, resulted in a strong autogenous temperature increase (beyond 100° C.), with consequent formation of a black gel, accompanied by formation of fumes. To check whether this exothermal state was caused, among other things, by a concurrent reaction, some sulfuric acid was added dropwise onto a column of acetonitrile in a test tube. An uncontrolled reaction with temperature increase occurred, with escape of part of the reaction mixture from the test tube and formation of a gelatinous yellow product. The solidification originates from polymerisation of the acetonitrile. In an industrial plant, this situation (reaction controlled by mass transfer i.e. when sulfuric acid is added little by little to a mixture of acetonitrile and halogen adamantane—or vice versa) can lead to local accumulations of reagent because of insufficient mixing. This leads to the possibility of heat peaks which are difficult to dissipate. The inventors of the present application have found that the Ritter reaction, if carried out with the reagents and in the proportions described in U.S. Pat. No. 3,391,142 develops a total exothermic heat of 890 kJ/mol, which—regardless of the further risk of heat peaks—is clearly excessive for standard reactors used in fine pharmaceutical chemistry.

There was therefore the problem of lowering heat development and of suppressing as far as possible the concurrent acetonitrile polymerisation reaction.

These objectives have been achieved by the new process described herein which minimizes the quantity of sulfuric acid (in U.S. Pat. No. 3,391,142, 24 equivalents were used), the quantity of acetonitrile (which even though used in gauged excess, is no longer consumed by the concurrent reaction) as well as the quantity of exothermal heat developed.

In accordance with a particularly preferred embodiment of the new process, usable for example for the synthesis of 1-acetamido-3,5-dimethyladamantane starting from 1-chloro-3,5-dimethyladamantane, 5-10 but preferably 6-8 equivalents of acetonitrile are used as well as 5-20 but preferably 6-8 equivalents of glacial acetic acid and 3-10 but preferably 3-5 equivalents of concentrated sulfuric acid. The aforesaid proportions apply both if, in step (b1), the sulfuric acid is introduced into the reaction mixture comprising acetonitrile, obtained in step (a1), and if, in step (b2), the acetonitrile is introduced into the reaction mixture comprising sulfuric acid, obtained in step (a2). Preferably, in step (b1) or (b2), the concentrated sulfuric acid or the acetonitrile is added to the reaction mixture at a rate such that in both cases a temperature of 50° C.-90° C. but preferably 70±5° C. is maintained during the reaction. This is because the inventors of the present application have found that at temperatures lower than 50° C., a reagent accumulation phenomenon can be observed (around 16%) with risk of exothermic triggering. On the other hand, at temperatures above 90° C. (critical value), the acetonitrile polymerisation phenomenon acquires considerable importance and results in a no longer quantitative consumption of the initially used halogen aminoadamantane as well as in a considerable increase in viscosity of the reaction mixture which also darkens in colour.

In contrast, under the specific conditions found by the inventors of the present application, total exothermic heat can be drastically reduced in this reaction (in the specific case of 1-acetamido-3,5-dimethyladamantane, even down to around 200 kJ/mol), this being a manageable value from the plant aspect without involving special expedients (the accumulation of reagents does not exceed about 5% when working at 70±5° C.) and the reaction of the halogen adamantane is almost quantitative which results in an easily isolatable and very pure product, obtainable at high yield with melting point of 113°-114° C. On the other hand, U.S. Pat. No. 3,391,142 mention about 97° C.

With regard to isolating the obtained acetamido adamantane, the cooled reacted mixture is introduced, preferably maintaining the temperature below 25° C., into a biphasic water/water-immiscible organic solvent (aliphatic or aromatic) washing system, for example water/toluene, from which the strongly acid aqueous phase is then discarded. The desired product remains, after further optional washes with water and/or 10% potassium bicarbonate solution, in the toluene phase from which it can be released by concentration under vacuum, to be available for the subsequent hydrolysis phase. The achievable GC purity is around 99.0%, with a maximum presence of 0.2% unreacted halogenide that is nevertheless totally removed during final purification provided in the next step. Achievable yields fluctuate between 92.5% and 97%.

The inventors of the present application have also found that the subsequent hydrolysis of the acetamido adamantanes of formula II to provide the corresponding aminoadamantanes of formula I can be conducted in standard equipment used in the field of proprietary drug synthesis if undertaken under the conditions described herein, in particular comprising the following steps:

(a) feeding into a reaction vessel a mixture comprising acetamido adamantane of formula II, 5-20 equivalents of an alkali metal or alkaline earth metal hydroxide and a solvent chosen from the group consisting of 1-methoxy-2-propanol, 2-methoxy-1-propanol, 3-methoxy-1-propanol, 2-ethoxyethanol, 2-methoxyethanol and mixtures thereof, to provide a hydrolysis mixture, (b) heating the hydrolysis mixture under reflux for a time sufficient to achieve hydrolysis of the acetamido adamantane of formula II to give the corresponding aminoadamantane of formula I, and (c) isolating the aminoadamantane of formula I formed in step (b).

Besides not requiring special plants, the aforesaid conditions do not cause degradation of the components of the hydrolysis mixture, so facilitating purification of the final product.

As aforementioned, the solvents used in the hydrolysis step according to the present invention are chosen from 1-methoxy-2-propanol, 2-methoxy-1-propanol, 3-methoxy-1-propanol, 2-ethoxyethanol, 2-methoxyethanol and mixtures thereof. Of the latter, 1-methoxy-2-propanol (propylene glycol monomethyl ether) is preferred. The solvent is preferably used in a quantity of at least 4 equivalents, preferably 4-20 equivalents. Of the alkali metal or alkaline earth metal hydroxides, sodium hydroxide micropearls are particularly preferred. A particle size of 1-3 mm is especially preferred.

In heating under reflux as in step (b), $\frac{1}{5}$-$\frac{1}{3}$ of the solvent volume used is preferably distilled off to raise the initial reflux temperature and remove any toluene residues.

Using the aforesaid solvents, preferably 1-methoxy-2-propanol, 2-methoxy-1-propanol, 3-methoxy-1-propanol, 2-ethoxyethanol, 2-methoxyethanol, but even more preferably 1-methoxy-2-propanol, in the hydrolysis mixture of the present invention, also leads to the further advantage of considerably facilitating isolation of the crude aminoadamantane addition salt by allowing, under the conditions identified by the inventors of the present application, most of the salt load to be extracted from the hydrolysis mixture with water before proceeding to precipitate the crude aminoadamantane addition salt from the previously extracted hydrolysis mixture. Said crude aminoadamantane addition salt can then be purified by a simple step of converting the addition salt into the corresponding free base, and consequent re-conversion into the purified addition salt which is thus obtained with a purity (GC). greater than 99.0%, in particular greater than 99.5%, rendering it directly usable in the pharmaceutical field.

On the other hand, in the process according to U.S. Pat. No. 3,391,142, isolation of the crude aminoadamantane took place by completely dissolving the hydrolysis mixture in water and subsequently re-extracting the aminoadamantane with five portions of benzene. After this, the crude aminoadamantane was transferred from benzene into ether, and from there precipitated as its semi-crude addition salt. The semi-crude addition salt thus obtained was then re-crystallized in its turn from a mixture of alcohol and ether to provide the purified addition salt.

Conversely, in accordance with a preferred embodiment of the hydrolysis step, particularly suited to the synthesis of crude memantine HCl, 1-methoxy-2-propanol is used as the hydrolysis solvent, proceeding with at least 6 but preferably at least 9 equivalents of alkali metal hydroxide, in particular 1-3 mm sodium hydroxide micropearls. Under these conditions, the reflux temperature under ordinary pressure stabilizes after an initial step in which the toluene residues, introduced by using the wet acetamido derivative, are distilled off at around 130° C., a temperature easily achievable in standard industrial plants.

After completion of the reaction (GC), the hydrolysis mixture is allowed to cool and then extracted with water while still hot (preferably 80±5° C.), the aqueous phase being discharged. Subsequently, at least two thirds of the organic phase are distilled off in order to remove the dissolved water. The crude aminoadamantane addition salt is then precipitated by adding HCl in isobutanol, preferably in two steps (firstly lowering the pH of the organic phase to less than 10.0, then to less than 2.0), diluting, between the two steps, with acetone in order to counteract the immediate formation of a very thick suspension.

The crude aminoadamantane addition salt as aforesaid can then be conveniently purified by adding a water immiscible organic solvent (the solvent can be aromatic, aliphatic or cycloaliphatic, n-heptane being preferably used), followed by addition of an aqueous alkaline solution (e.g. 50% by weight of potassium hydroxide), in order to release the aminoadamantane from its addition salt and favour the migration of the free base into the organic phase. To this end, a pH of at least 12.0 is preferably established in the aqueous phase. After discharging the alkaline aqueous phase, the organic phase is then filtered, concentrated under vacuum and the concentrate diluted with acetone or MIBK, MEK or C1-C6 linear or branched alcohols. By adding HCl in isobutanol the purified aminoadamantane addition salt is then precipitated from the ketonic or alcoholic, preferably acetonic, solution.

The total yield of the process described herein from the halogen adamantane to the purified aminoadamantane addition salt is around 82%.

EXAMPLES

Example 1

| Synthesis of 1-acetamido adamantane | | | | | |
|---|---|---|---|---|---|
| RAW MATERIALS | d (g/ml) | g | ml | mols | MR |
| 1-CHLORO-3,5-DI-METHYLADAMANTANE | | 150.0 | | 0.755 | 1.00 |
| ACETONITRILE | 0.782 | 215.05 | 275.0 | 5.239• | 6.95• |
| SULFURIC ACID 95-97% | 1.83 | 305.28 | 165.9 | 3.0192 | 4.00 |
| GLACIAL ACETIC ACID | 1.05 | 288.75 | 275.0 | 4.808• | 6.37• |
| DEION. WATER (QUENCHING) | | 1500.0 | 1500.0 | • | • |
| TOLUENE (EXTRACTION) | 0.87 | 1305.0 | 1500.0 | • | • |
| DEION. WATER (WASHING) | 1.00 | 750.0 | 750.0 | • | • |
| 10% KHCO$_3$ SOL. (WASHING) | | 750.0 | | • | • |

Pilot Process on Laboratory Scale

The 1-chloro-3,5-dimethyladamantane (viscous liquid), the acetonitrile and the glacial acetic acid are fed into a 2 liter glass reactor at room temperature. The solution is heated to Ti=70±5° C. and, maintaining this temperature, the sulfuric acid is added dropwise over at least four hours while maintaining the temperature range. During the dropwise addition of the acid, the reaction is exothermic. At the end of the addition, the mixture is left at Ti=70±5° C. and the end of the reaction is monitored by GC. The mixture is then cooled to Ti=25±5° C. In the round bottom quench flask the water, cooled to 5/10° C., and the extraction toluene are prepared. While maintaining the T<25° C. the mixture in the reactor is poured into the water-toluene system. Agitation is applied for 15 minutes then the phases are allowed to separate for at least 30 minutes. The very acid aqueous phase is drawn off and discarded, and the organic phase is washed first with water then with a 10% potassium bicarbonate solution. The phases are again allowed to separate for at least 30 minutes. The lower aqueous phase is discarded and the toluene solution is completely clarified by filtering through a dicalite panel.

The clear filtrate is fed into the flask where the subsequent hydrolysis is carried out. The toluene is concentrated by concentration under vacuum until a stirrable residue is obtained. This residue is used as such for the next step.

Yield obtained=162.15 g 1-acetamido-3,5-dimethyl-adamantane (white solid).

Theoretical yield=167.07 g equal to a yield=97.05%.

Melting point 113-114° C. GC purity >99.0%.

Example 2

Obtaining crude memantine hydrochloride

| RAW MATERIALS | d (g/ml) | g | ml | moles | RM |
|---|---|---|---|---|---|
| TOLUENIC SOL. 1-ACETAMIDO-3,5-DIMETHYL-ADAMANTANE | | 292 g wet corresponding to 162.15 g dry | | 0.7325 | 1.00 |
| 1-METHOXY-2-PROPANOL | 0.920 | 874.0 | 950.0 | 9.70 | 13.24 |
| SODIUM HYDROXIDE MICROPEARLS | | 263.7 | | 6.5925 | 9.00 |
| DEIONIZED WATER | 1.00 | 550.0 | 550.0 | • | • |
| approx 20% HCL IN ISO-BUTOH, $1^{ST}$ ADDITION | 0.890 | 169.1 | 190.0 | | |
| ACETONE | 0.792 | 613.8 | 775.0 | • | • |
| approx 20% HCL IN ISO-BUTOH, $2^{ND}$ ADDITION. | 0.890 | 35.6 | 40.0 | | |
| ACETONE (FINAL WASHING) | 0.792 | 87.1 | 110.0 | • | • |

Pilot Process on Laboratory Scale

Sodium hydroxide micropearls and 1-methyoxy-2-propanol are fed into a 3-liter flask containing the 1-acetamido-3,5-dimethyladamantane toluenic concentrate obtained above. The mixture is refluxed, distilling off the first 150 ml of solvent. The initial reflux temperature is around 105° C., but after removing the overheads it will rise to around 130° C. On reaching 130° C. it is maintained under reflux for 6/8 hours. The dark coloured mixture is cooled to Ti=80±5° C. and the end of reaction checked by GC.

| Hours of reaction | Unreacted 1-acetamido-3,5-dimethyladamantane (%) |
|---|---|
| 3 | 11.86 |
| 4 | 3.90 |
| 5 | 1.47 |
| 6 | 0.29 |

On termination of hydrolysis, the mixture is cooled to Ti=80±5° C. and 550 ml of deionised water are carefully introduced; the mixture is left under agitation for a few minutes until complete dissolution. The two phases are left to separate at Ti=80±5° C. for at least one hour. The underlying dark and very alkaline phase is poured off and discarded. The stirrer is inserted and at least 600 ml of solvent are distilled off under vacuum to remove all the water present in the system. At the end of the concentration the residue is cooled to Ti=20±5° C., then while maintaining the temperature range the first aliquot of 190 ml 20% hydrochloric acid in isobutanol is added drop-wise such that the pH<10. A very thick paste is obtained because of massive precipitation of the memantine hydrochloride and the inorganic chlorides. At this point the mixture is diluted with caetone and while maintaining Ti=20±5° C., the pH is adjusted to 2.0±0.5 with about 40 ml of 20% hydrochloric acid in isobutanol, leaving under agitation at Ti=20±5° C. for at least one hour and again checking the pH, possibly making small corrections using the hydrochloric acid solution. The suspension is cooled to Ti=0±5° C. for at least one hour, filtered and the solid washed with acetone. 240.4 g of crude hydrochloride are obtained. The product is used wet for the subsequent step. The weight of crude hydrochloride obtained, if dried, is greater than the theoretical. This is because it precipitates in the presence of considerable quantities of inorganic salts (sodium chloride and sodium acetate). GC purity of the crude hydrochloric is already 99.78%-99.90%.

Example 3

Purification of the memantine hydrochloride

| RAW MATERIALS | (g/ml) | g | ml | mols | RM |
|---|---|---|---|---|---|
| WET CRUDE MEMANTINE HCL | | 240.4 | | 0.7156 (estimate) | 1.00 |
| DEIONIZED WATER | 1.00 | 1235.0 | 1235.0 | | |
| 50% POTASSIUM HYDROXIDE SOL. BY WEIGHT | 1.51 | 96.4 | 63.8 | 0.859 | 1.20 |
| N-HEPTANE (EXTRACTION) | 0.683 | 632.5 | 926.0 | | |
| N-HEPTANE (FILTER WASHING) | 0.683 | 68.3 | 100.0 | | |
| ACETONE (BASIC DILUTION) | 0.792 | 1164.2 | 1470.0 | | |
| HCL IN ISOBUTOH ≈ 20% | 0.89 | 115.7 | 130.0 | | |
| ACETONE (WASHING) | 0.792 | 95.0 | 120.0 | | |

Pilot Procedure on Laboratory Scale

The crude wet hydrochloride and the deionised water are fed into a three liter flask. The stirrer is inserted and the mixture left for some minutes at ambient temperature; the n-heptane is added and the 50% potassium hydroxide solution added in a thin stream. The biphasic system is stirred at Ti=25±5° C. for about 30 minutes and the pH checked for >12.0; stirring is halted and the phases left to separate for at least one hour.

The underlying aqueous phase is separated and removed, the organic phase is perfectly clarified by filtration then added to the flask for final hydrochloride precipitation. The filter is washed with 100 ml of n-heptane and the wash liquid is combined with the main solution. The basic memantine solution is concentrated under vacuum to at least half volume and cooled to Ti=20±5° C. The concentrate is diluted with 1470 ml of acetone and the final hydrochloride is precipitated by adding 20% hydrochloric acid in isobutanol until the pH is stable at 2.5±0.5. The suspension is cooled to Ti=0±5° C. for at least one hour, the final hydrochloride is filtered off and washed with acetone. 215.0 g of a white wet product are obtained. It is dried in an oven under vacuum at Ti=60±5° C. for at least 10 hours.

Yield=133.3 g of dry product.

Total theoretical yield calculated from 150 g of initial 1-chloro-3,5-dimethyladamantane=162.8 g of memantine hydrochloride.

Total process yield=81.8%.

The final product is very pure by GC (>99.5%).

What is claimed is:

1. Process for synthesizing acetamido adamantanes of formula II

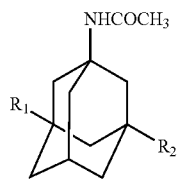

in which R1 and R2 are identical or different, and are H or a straight or branched alkyl group, comprising from 1 to 6 carbon atoms, from a halogen adamantane of formula III

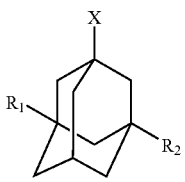

in which R1 and R2 are as above, and in which X is F, Cl, Br or I, comprising the following steps:
  (a1) feeding into a reaction vessel a mixture comprising the halogen adamantane of formula III, 5-10 equivalents of acetonitrile and 5-20 equivalents of glacial acetic acid, to provide a reaction mixture,
  (b1) introducing into the reaction mixture 3-10 equivalents of concentrated sulfuric acid, to provide a reacted mixture, or, alternatively:
  (a2) feeding into a reaction vessel a mixture comprising the halogen adamantane of formula III, 5-20 equivalents of glacial acetic acid and 3-10 equivalents of concentrated sulfuric acid, to provide a reaction mixture,
  (b2) introducing into the reaction mixture 5-10 equivalents of acetonitrile to provide a reacted mixture, and
  (c) isolating the acetamido adamantane of formula II formed in step (b1) or (b2) from the reacted mixture,
  wherein a reaction temperature of 50° C.-90° C. is maintained during introduction of sulfuric acid or of acetonitrile in step (b1) or (b2).

2. Process as claimed in claim 1, wherein 6-8 equivalents of acetonitrile, 6-8 equivalents of glacial acetic acid and 3-5 equivalents of concentrated sulfuric acid are used, with reference to the halogen adamantane of formula III.

3. Process as claimed in claim 1, wherein a reaction temperature of 70±5° C. is maintained during introduction of sulfuric acid or of acetonitrile in step (b1) or (b2).

4. Process as claimed in claim 1, wherein the halogen adamantane used in step (a1) or (a2) is 1-halogen-3,5-dimethyladamantane in which the halogen residue is chosen from the group consisting of F, Cl, Br and I, to give 1-acetamido-3,5-dimethyladamantane in step (c).

5. Process for synthesizing aminoadamantanes of formula I

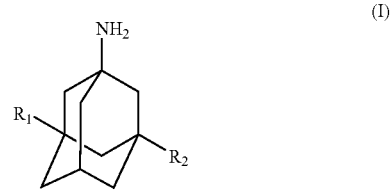

in which R1 and R2 are identical or different and are H or a straight or branched alkyl group comprising from 1 to 6 carbon atoms, from acetamido adamantane of formula II

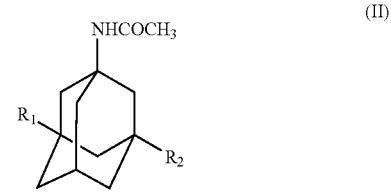

in which R1 and R2 are as aforestated, comprising the following stages:

stage 1) synthesizing acetamido adamantanes of formula II from a halogen adamantine of formula III

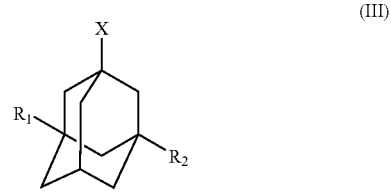

in which R1 and R2 are as above, and in which X is F, Cl, Br or I, through the following steps:
  (a1) feeding into a reaction vessel a mixture comprising the halogen adamantane of formula III, 5-10 equivalents of acetonitrile and 5-20 equivalents of glacial acetic acid, to provide a reaction mixture,
  (b1) introducing into the reaction mixture 3-10 equivalents of concentrated sulfuric acid, to provide a reacted mixture, or alternatively:
  (a2) feeding into the reaction vessel a mixture comprising the halogen adamantine of formula III, 5-20 equivalents of glacial acetic acid and 3-10 equivalents of concentrated sulfuric acid, to provide a reaction mixture,
  (b2) introducing into the reaction mixture 5-10 equivalents of acetonitrile to provide a reacted mixture, and
  (c) isolating the acetamido adamantine of formula II formed in step (b1) or (b2) from the reacted mixture;
  wherein a reaction temperature of 50° C.-90° C. is maintained during introduction of sulfuric acid or of acetonitrile in step (b1) or (b2); and stage 2) synthesizing aminoadamantanes of formula I from acetamido adamantane of formula II of stage 1) through the following steps:
(a) feeding into a reaction vessel a mixture comprising acetamido adamantane of formula II, 5-20 equivalents of an alkali metal or alkaline earth metal hydroxide and a solvent chosen from the group consisting of 1-methoxy-2-propanol, 2-methoxy-1-propanol, 3-methoxy-1-propanol, 2-ethoxyethanol, 2-methoxyethanol and mixtures thereof, to provide a hydrolysis mixture,
(b) heating the hydrolysis mixture under reflux for a time sufficient to achieve hydrolysis of the acetamido adamantane of formula II to give the corresponding aminoadamantane of formula I, and
(c) isolating the aminoadamantane of formula I formed in step (b), preferably by conversion into an addition salt thereof.

6. Process as claimed in claim 5, wherein in stage 1) 6-8 equivalents of acetonitrile, 6-8 equivalents of glacial acetic acid and 3-5 equivalents of concentrated sulfuric acid are used, with reference to the halogen adamantane of formula III.

7. Process as claimed in claim 5, wherein a reaction temperature of 70±5° C. is maintained during introduction of sulfuric acid or of acetonitrile in step (b1) or (b2).

8. Process as claimed in claim 5, wherein the halogen adamantane used in step (a1) or (a2) is 1-halogen-3,5-dimethyladamantane, in which the halogen residue is chosen from the group consisting of F, Cl, Br, and I, to give 1-acetamido-3,5-dimethyladamantane in step (c) of stage 1).

9. Process as claimed in claim 5, wherein the solvent of step (a) of stage 2) is 1-methoxy-2-propanol.

10. Process as claimed in claim 9, wherein in step (a) at least 4 equivalents, but preferably 4-20 equivalents of solvent are used.

11. Process as claimed in claim 5, wherein in step (a) at least 6 but preferably 9 equivalents of alkali metal hydroxide are used.

12. Process as claimed in claim 5, wherein the alkali metal hydroxide used is sodium hydroxide.

13. Process as claimed in claim 5, wherein the alkali metal hydroxide is used as pearls of 1-3 mm diameter.

14. Process as claimed in claim 5, wherein in step (b) $1/7$-$1/5$ of the solvent volume used is initially distilled off.

15. Process as claimed in claim 5, wherein step (c) itself of stage 2) comprises the following steps:
(c1) extracting the hydrolysis mixture with water,
(c2) discarding the aqueous phase,
(c3) precipitating from the organic phase the formed aminoadamantane addition salt of formula I by adding an organic or inorganic acid, and
(c4) purifying the aminoadamantane addition salt of formula I by re-precipitation.

16. Process as claimed in claim 15, wherein the extraction of step (c1) is carried out at a temperature of 80±5° C.

17. Process as claimed in claim 15, wherein after the discarding at step (c2) at least half of the organic phase is distilled off and the distillate discarded.

18. Process as claimed in claim 15, wherein the re-precipitation of step (c4) itself comprises the following steps:
(c41) adding a water-immiscible aromatic, aliphatic or cycloaliphatic organic solvent to the aminoadamantane addition salt of formula I to give a suspension,
(c42) adding an aqueous alkaline solution to the suspension formed,
(c43) discarding the aqueous phase,
(c44) filtering and concentrating the organic phase,
(c45) diluting the organic phase with a solvent chosen from the group consisting of acetone, MIBK, MEK and linear or branched C1-C6 alcohols, and
(c46) precipitating the aminoadamantane addition salt of formula I by adding an organic or inorganic acid.

19. Process as claimed in claim 18, wherein the aliphatic solvent used in step (c41) is n-heptane.

20. Process as claimed in claim 18, wherein the solvent used in step (c45) is acetone.

21. Process as claimed in claim 5, wherein the amino adamantane is memantine hydrochloride.

* * * * *